United States Patent [19]

Rutkowski

[11] Patent Number: 6,047,591
[45] Date of Patent: Apr. 11, 2000

[54] CORROSION RING GAUGE AND METHOD

[75] Inventor: Anthony J. Rutkowski, Glendora, N.J.

[73] Assignee: Sunoco, Inc. (R&M), Philadelphia, Pa.

[21] Appl. No.: 09/256,675

[22] Filed: Feb. 23, 1999

[51] Int. Cl.[7] ........................................ G01N 17/00
[52] U.S. Cl. ........................................................ 73/86
[58] Field of Search ...................... 73/86, 865.8; 33/562, 33/563, 567, 555.1

[56] References Cited

U.S. PATENT DOCUMENTS

| | | | |
|---|---|---|---|
| 5,447,057 | 9/1995 | Shaw et al. | 73/86 |
| 5,739,424 | 4/1998 | Beavers | 73/86 |

*Primary Examiner*—Robert Raevis
*Attorney, Agent, or Firm*—Robert A. Koons, Jr.; Kenneth Crimaldi; Pepper Hamilton LLP

[57] ABSTRACT

The invention is a corrosion ring gauge for evaluating the limit of allowable corrosion on the mated surfaces defining the gasket seating area of a bolted pipe flange, and a method for performing the evaluation. The invention includes a ring having an interior edge corresponding to the allowable radial corrosion advancement on a mated surface when the ring is centered on the mated surface. Attached to the ring are at least two centering pins, each of which is aligned with the position of a bolt bore on the flange when the ring is centered on a mated surface. The method of the invention involves centering the corrosion ring gauge on a mated surface and marking the location of the interior edge of the ring on the mated surface. After removing the corrosion ring gauge from the mated surface, a straight edge is positioned on the mated surface so that it intersects the marked location. Light transmitting between the straight edge and mated surface is detected to determine if light is transmitted radially beyond said marked location.

3 Claims, 2 Drawing Sheets

CORROSION RING GAUGE AND METHOD

FIELD OF THE INVENTION

The invention relates to a gauge useful for evaluating whether the limit of allowable corrosion on the mated surfaces of a raised face pipe flange have been exceeded, and a method for performing the evaluation.

BACKGROUND OF THE INVENTION

Raised face (RF) pipe flanges used in corrosive services can experience corrosion on the mated surfaces of the flange. If left unchecked, the corrosion can result in failure of the flange and the leakage of hazardous corrosive materials. To prevent such occurrences, RF flanges in corrosive services are routinely inspected for the progression of corrosion on the mated surfaces, and are replaced when the corrosion extends beyond an acceptable position on the mated surfaces.

Typically, flange corrosion inspections consist of a simple visual evaluation of the radial corrosion on the mated faces. However, such inspections leave much to the judgement of the inspector, which can lead to inconsistent evaluations. The inspection process would benefit from a device and method that could simplify and bring consistency to the inspection process.

SUMMARY OF THE INVENTION

Briefly, the invention is a corrosion ring gauge for evaluating the limit of allowable corrosion on the mated surfaces of a bolted RF pipe flange, and a method for performing the evaluation. The invention comprises a ring having an interior edge corresponding to the allowable radial corrosion advancement on a mated surface when the ring is centered on the mated surface. Attached to the ring are at least two centering pins, each of which is aligned with the position of a bolt bore on the flange when the ring is centered on a mated surface. The bolt bores serve as guides for the centering pins so that the ring can be quickly and reliably centered on the mated surface.

The method of the invention involves centering the corrosion ring gauge on a mated surface and marking the location of the interior edge of the ring on the mated surface. After removing the corrosion ring gauge from the mated surface, a straight edge is positioned on the mated surface so that it intersects the marked location. Light transmitted between the straight edge and mated surface is detected to determine if light is transmitted radially beyond said marked location. Light transmitted radially beyond the marked location indicates that corrosion has threatened the integrity of the flange seal.

DETAILED DESCRIPTION OF THE INVENTION

Applicants have discovered a corrosion ring gauge and method that both simplifies and improves the accuracy of the inspection process for bolted RF pipe flanges. The corrosion ring gauge is an elegantly simple device comprising a ring and at least two centering pins. The interior edge of the ring is equal to the allowable radial corrosion advancement on a mated surface of the flange when the ring portion is centered on the mated surface. "Mated surface" refers to either opposed surface of the RF flange on which the sealing element (typically a gasket) is seated. The centering pins are attached to the ring and correspond to the position of the bores in the flange that receive the bolts when the ring portion is centered on the mated surface. Accordingly, the corrosion ring gauge can be quickly and easily centered on the mated surface of the flange by aligning the centering pins with the appropriate bolt bores of the flange.

The materials used in the fabrication of the corrosion ring gauge are not particularly limited. Preferably, the corrosion ring gauge is made of a durable, dimensionally-stable material, such as steel. The dimensions of the corrosion ring gauge (other than the interior edge) can vary widely, so long as 1) the device can be centered on the mated surface by engaging the centering pins with the appropriate bolt bores, and 2) the position of the inner diameter can be marked on the mated surface when the centering pins are so engaged.

The centering pins are attached to the ring. The term "attached" encompasses all methods of attachment as well as integral formation of centering pins with the ring, such as through molding, casting, forging or other techniques.

As described above, the method of the invention involves centering the corrosion ring gauge on a mated surface and marking the location of the interior edge of the ring on the mated surface. After removing the corrosion ring gauge from the mated surface, a straight edge is positioned on the mated surface so that it intersects the marked location. Light transmitting between the straight edge and mated surface is detected to determine if light is transmitted radially beyond said marked location. Light transmitted radially beyond the marked location indicates that corrosion has threatened the integrity of the flange seal.

The step of marking the location of the inner diameter of the ring on the mated surface can be accomplished by any marking technique. The type of straight edge utilized in the method is not particularly limited. Similarly, the method and/or device for detecting light transmission between the straight edge and mated surface beyond the marked position is not particularly limited, and may simply comprise human observation.

The invention will now be described with reference to drawings illustrating a preferred embodiment. The drawings are not intended to limit the scope of the invention defined in the appended claims.

Figure 1:
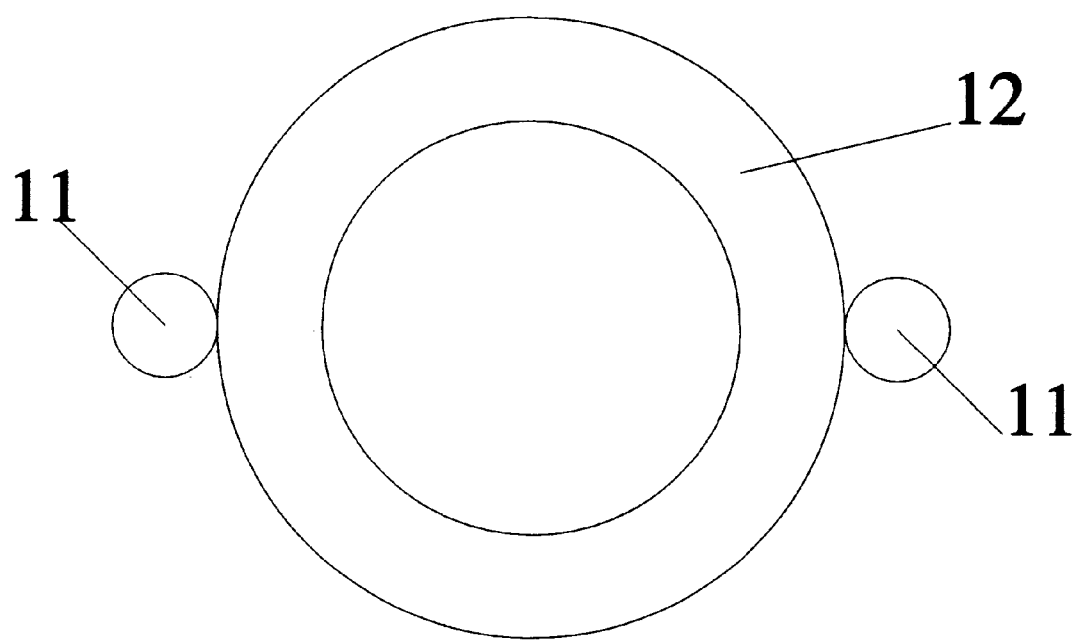
FIG. 1 is a plan view of a corrosion ring gauge in accordance with the invention.
Figure 2:
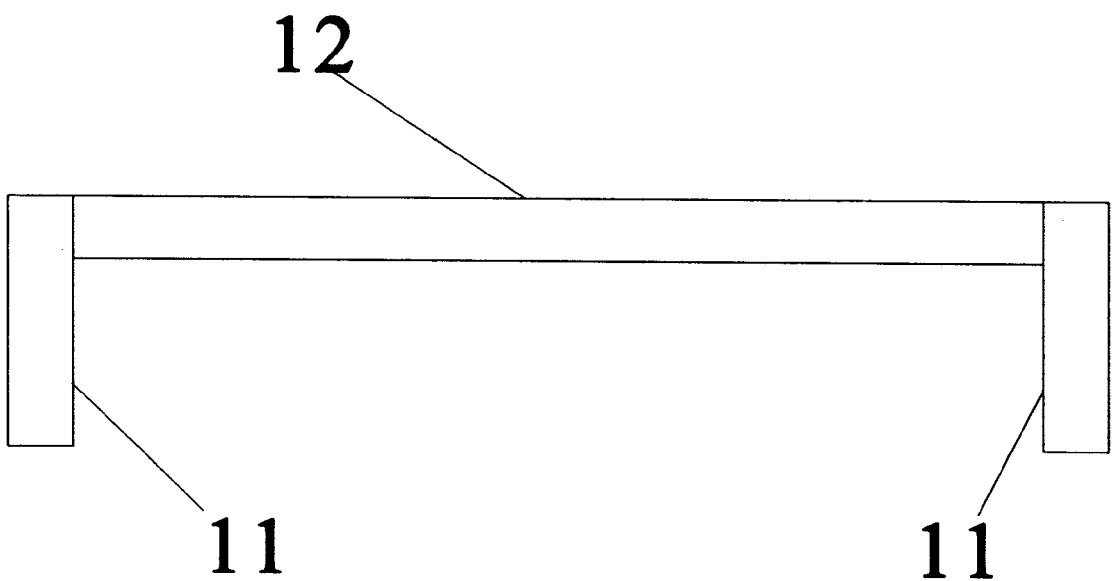
FIG. 2 is an elevation view of the corrosion ring gauge depicted in FIG. 1.

FIG. 1 and FIG. 2 are plan and elevation views, respectively, of a corrosion ring gauge in accordance with the invention. Two centering pins 11 are attached to ring 12. Centering pins 11 extend in a substantially perpendicular direction to ring 12 and correspond to the position and size of two bolt bores in a bolted RF flange (not shown). Ring 11 is centered on the mated face of the flange when centering pins 11 are engaged with the bolt bores. The interior edge of ring 12 corresponds to the allowable corrosion in a radial direction on the mated surface of the flange when ring 12 is centered on the mated surface.

Though the invention has been described above with reference to specific embodiments, other embodiments of the invention can readily be envisioned by one of ordinary skill in the art in light of this teaching. Modifications, substitutions, changes and/or omissions may be made without departing from the spirit and scope of the invention defined in the appended claims.

What is claimed is:

1. An apparatus for indicating the limit of allowable corrosion on a mated surface of a bolted raised face pipe flange, said pipe flange having a longitudinal axis substantially perpendicular to said mated surface, said apparatus comprising:

a) a ring, said ring having an interior edge corresponding to the allowable radial corrosion advancement on said mated surface when said ring is positioned on said mated surface and centered about said longitudinal axis; and b) at least two centering pins attached to said ring and extending in a direction substantially parallel to said longitudinal axis, wherein the position of at least a portion of each of said centering pins corresponds to a bolt location on said pipe flange when said ring is positioned on said mated surface and centered about said longitudinal axis.

2. The apparatus according to claim 1, wherein said centering pins are substantially the same diameter as the bolts corresponding to said bolt locations.

3. A method of evaluating the advancement of radial corrosion on a mated surface of a pipe flange, said pipe flange having a longitudinal axis substantially perpendicular to said mated surface, said method comprising the steps of:

a) centering a ring on said mated surface about said longitudinal axis, said ring having an interior edge corresponding to the allowable radial corrosion advancement on said mated surface;

b) marking the location of said interior edge of said ring on said mated surface;

c) removing said ring from said mated surface;

d) positioning a straight edge on said mated surface so that it intersects said marked location of said interior edge of said ring;

e) detecting the transmittance of light between said straight edge and said mated surface to determine if light is transmitted between said straight edge and said mated surface in a region radially beyond said marked location.

* * * * *